United States Patent [19]

Davis et al.

[11] 4,153,691

[45] May 8, 1979

[54] ANALGESIC AND ANTI-INFLAMMATORY COMPOSITIONS

[75] Inventors: Adrian F. Davis, Feltham; Gordon J. A. Dixon, Surbiton, both of England

[73] Assignee: Beecham Group Limited, United Kingdom

[21] Appl. No.: 769,428

[22] Filed: Feb. 17, 1977

[30] Foreign Application Priority Data

Feb. 20, 1976 [GB] United Kingdom ................. 6716/76

[51] Int. Cl.$^2$ .................... A61U 31/60; A61U 31/625
[52] U.S. Cl. ..................................... 424/230; 424/232
[58] Field of Search ................................ 424/230, 232

[56] References Cited

PUBLICATIONS

Grollman, Pharmacology & Therapeutics, 6th ed. (1965), pp. 166–175.
S. Pasquino, Boll. Chem. Farm, 1957, 96, pp. 47–50.
Anschütz et al., Ann. (1924), 439, 1, pp. 5–7.

Primary Examiner—Stanley J. Friedman
Attorney, Agent, or Firm—Jacobs & Jacobs

[57] ABSTRACT

A pharmaceutical composition having analgesic, antipyretic and anti-inflammatory activity and administration thereof in oral dosage form, comprising 2-(carbamoyl)phenyl-2-acetoxybenzoate as active ingredient and procedure for preparing such active ingredient. One or more pharmaceutically acceptable oral carriers are mixed with the active ingredient for oral administration in various dosage forms. The disadvantages of acetyl salicyclic acid and salicylamide are avoided.

6 Claims, No Drawings

ANALGESIC AND ANTI-INFLAMMATORY COMPOSITIONS

This invention relates to pharmaceutical compositions having analgesic, antipyretic and anti-inflammatory activity in mammals, including man. The invention further concerns a process for the preparation of the pharmaceutical compositions and the active component of the compositions, namely 2(carbamoyl)phenyl-2-acetoxybenzoate.

BACKGROUND OF THE INVENTION

Acetyl salicyclic acid (aspirin) is a widely used analgesic, antipyretic and anti-inflammatory drug, but it causes bleeding in the upper gastro-intestinal tract following oral administration. In most cases such bleeding is so slight as to be harmless, but it can be a major problem in some patients especially those who regularly take high doses, for example those who suffer from rheumatoid disease.

O-hydroxybenzamide (salicylamide) is also a known analgesic, antipyretic and anti-inflammatory drug. Salicylamide does not appear to cause gastro-intestinal bleeding, but unfortunately suffers from other disadvantages, the most significant being extensive inactivation by various metabolic processes in the gastrointestinal mucosal cells and liver. It appears that inactivation is due to conjugation of the phenolic hydroxyl group with sulphate and glucuronic acid. In man, approximately 1.5 gms of salicylamide must be consumed before the enzymes responsible for this conjugation are saturated and significant quantities of unmetabolised salicylamide pass into bloodstream to exert pharmacological action.

Despite these drawbacks, aspirin and salicylamide are widely used, both singly and in purely physical mixtures.

The salicylamide ester of aspirin was prepared by two routes by Anschütz and Reipenkröger (Ann.(1924) 439,1,pp.5-7) but these authors were concerned only with the chemistry of the substances and its preparation. Certainly the publication contains no hint of the possible pharmacological properties of the ester.

DESCRIPTION OF THE INVENTION

We have prepared the salicylamide ester of aspirin and we find that it is stable for long periods in acid at the pH encountered in the stomach, yet is rapidly enzymatically hydrolysed in blood. Although it appears to have little or no analgesic, antipyretic or anti-inflammatory activity in its own right, it is absorbed from the gastrointestinal tract into the blood, where it is hydrolysed to the active species. The gastro-intestinal bleeding problems associated with aspirin and the extensive inactivation problems of salicylamide are not encountered with the condensation product. The known synergy between aspirin and salicylamide can be more readily exploited with the condensation product than with simple mixtures, since it is not necessary to give the high doses of salicylamide which would otherwise be required to overcome its metabolic inactivation.

Accordingly, the present invention provides a pharmaceutical composition adapted for oral administration to human beings comprising 2-(carbamoyl)phenyl-2-acetoxybenzoate of formula (I).

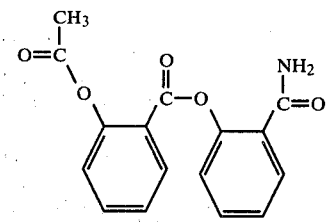

and one or more pharmaceutically acceptable oral carriers.

The compositions of the invention may be in the form of capsules, pills, tablets or aqueous suspensions, or powders for addition to, and suspension in water. Effervescent tablets or powders may be prepared by including a conventional effervescent couple in the formulation. The compositions include one or more pharmaceutical carriers for the active ingredient, such as diluents, binders, disintegrants, powder-flow aids and the like, in accordance with normal pharmaceutical practice. Additional excipients such as colour, flavours, wetting agents and the like may also be present if desired.

The invention also includes a process for the preparation of an analgesic and anti-inflammatory pharmaceutical composition comprising bringing 2-(carbamoyl)phenyl-2-acetoxybenzoate into a form adapted for oral administration to human beings.

The daily dose of 2-(carbamoyl)phenyl-2-acetoxybenzoate will vary according to the severity of the condition which is to be treated. For headaches, toothache and other minor aches and pains such as the symptoms of colds and influenza, a single dose of from 300 mg to 1 gm, or more preferably 500 mg. to 1 g, up to 3 times daily is suitable. For the treatment of more serious pain and inflammation such as rheumatoid disease (arthritis) a daily dose of from 2 gm to 8 gm, or more preferably 4 gm to 8 gm, would be more appropriate.

Thus, the invention further includes a method of treating pain and/or inflammation in human beings comprising the oral administration of an effective amount of 2-(carbamoyl)phenyl-2-acetoxybenzoate.

2-(Carbamoyl)phenyl-2-acetoxybenzoate can be prepared by reacting a salt of salicylamide with an acetyl salicylic acid halide, particularly the acid chloride. This reaction is preferably carried out in an inert organic liquid medium which is preferably eventually anhydrous. Suitable media include anhydrous toluene, benzene and chloroform. The salt of salicylamide may be one which is insoluble in the reaction medium, and in such cases, a solution of the acetyl salicylic acid halide would be added to a suspension of the salicylamide salt. Examples of salts of salicylamide include the alkali metal salts, especially the sodium salt. On occasions it may be possible to prepare the acid chloride in situ, as the reaction takes place. Since mild alkaline hydrolysis of 2-(carbamoyl)phenyl-2-acetoxybenzoate causes rearrangement to disalicylamide, the reaction conditions should be chosen to avoid or at least minimize this reaction. Similarly, heating of the compound in boiling water produces 2-(2'-hydroxyphenyl)-4H-1,3-benzoxazin-4-one and consequently the reaction conditions should be chosen to avoid this rearrangement product.

The following Example 1 illustrates the preparation of 2-(carbomoyl)phenyl-2-acetoxybenzonate:

EXAMPLE 1

Stage 1—Preparation of acetyl salicyloyl chloride

The acid chloride is prepared by reacting aspirin with an excess of thionyl chloride using urea to catalyse the reaction.

In a 2 liter, 3-neck flask equipped with a water bath, stirrer and thermometer is placed 200 ml of thionyl chloride (2.75 mols). To this is added about half the 360 g (2 mols) of aspirin. The fairly mobile suspension is stirred and warmed to 30° and 4 g of urea then added. Initiation of the reaction appears to be enhanced by minimal agitation. Evolution of HCl gas, and a fairly rapid fall in temperature indicate that the reaction has started, and a slow to medium stirring rate is then maintained. The temperature of the mixture is held at 25°. As mobility increases the remaining aspirin is fed in via a powder funnel in the third neck of the flask, fitted with a 'Y' piece, one arm leading to a gas outlet connected to a scrubber for absorbing HCl and $SO_2$. It is important to avoid the ingress of air containing moisture during this stage of the reaction. The completion of the reaction is indicated by the appearance of the reaction mixture which becomes a clear pale yellow fluid. At this stage a further 30 mins stirring at 25°-30° is given. This is followed by the addition of approximately 500 ml of 60°-80° petroleum ether at ca 30° with vigorous stirring. On cooling, the acid chloride is thrown out of solution as a heavy crystalline off-white solid. It is filtered off, washed with petroleum ether and dried quickly in a forced draught oven at 35°-40°. Exposure to air should be kept to a minimum.

The compound has a melting point of 47°-50°. The method can give a weight yield of about 90% of material, ca 93% pure (indicated by halogen estimation).

Stage 2—Preparation of 2-(Carbamoyl)phenyl-2-acetoxybenzoate 15 gm of spray dried sodium salicylamide was slurried with 100 ml of toluene, and stirred in an ice bath. To this was slowly added a solution of 20 gm of acetyl salicyloyl chloride dissolved in 75 ml of toluene. After approx. ½ hour the white precipitate is completely formed. This is filtered off and dried at 35°-40°. The reaction yields approx. 30 gm. of product. The dried compound is slurried with 250 ml of a saturated sodium bicarbonate solution which removes sodium chloride and excess salicyclate. The solid is then filtered off and dried again at 35°-40° followed by recrystallisation from an ethanol/methanol mixture. This yields white crystals which melt anywhere between 152°–170° C. depending on the method of assessment. The compound was soluble in water at room temperature to about 30 mg/100 ml. Thin layer chromatography and a negative ferric chloride test for phenol hydroxyl group showed that the product did not contain significant amounts of starting material. Infra red, ultra violet, nuclear magnetic resonance and mass spectra were consistent with the formula given earlier in this Specification.

Kinetic Studies in Plasma and Simulated Gastric Juices

Plasma 0.2 ml of a 5 mg/ml methanolic solution of 2-(carbamoyl)phenyl-2-acetoxybenzoate was added to 20 ml of fresh plasma at 37° C. (equivalent to adding 1 mg of compound, i.e. 50 mg/ml). 2 ml samples were removed at t=o, 5, 15, 30, 60 and 120 minutes and assayed for salicylic acid and salicylamide by extraction, silylation and G.L.C. analysis.

The results showed that hydrolysis had completely taken place by the time that the first 5 min. sample had been analysed.

Simulated Gastric Fluid

A similar experiment was carried out in 0.1 N HCl at 37° C. (the approximate stomach acid concentration) and the samples were assayed by the same procedure. The results showed very little degradation after four hours. The following Examples 2-5 illustrate pharmaceutical compositions adapted for oral administration to human beings, in accordance with the invention:

EXAMPLE 2

| Tablets | Parts Wt. |
| --- | --- |
| 2 (Carbamoyl) phenyl-2-acetoxybenzoate | 50 |
| Polyvinylpyrolidone (PVP) | 1 |
| Stearic acid | 1 |

2-(Carbamoyl)phenyl-2-acetoxybenzoate and half of the stearic acid are mixed and wet granulated with PVP solution. The resulting granules are sieved through a 16 mesh sieve and mixed with the rest of the stearic acid. The mix is then compressed on lozenge shaped punches to a weight of about 780 mg per tablet.

EXAMPLE 3

| Hard Gelatin Capsules | Parts Wt. | Parts Wt. |
| --- | --- | --- |
| Primojel (a starch disintegrant) | 1 | 1 |
| 2-(Carbamoyl) phenyl-2-acetoxy benzoate (micronised) | 32.33 | 30.66 |
| Lactose | — | 1.66 |
| Silica aerogel (Aerosil 200) | — | 0.08 |

In both cases the Primojel was dried overnight at 60° C. The ingredients were blended and the mixes filled into hard gelatin capsules, in amounts equivalent to 400 mg 2-(Carbamoyl)phenyl-2-acetoxybenzoate per capsule.

EXAMPLE 4

| Soft Gelatin Capsules | Parts Wt. |
| --- | --- |
| 2-(Carbamoyl) phenyl-2-acetoxy benzoate (micronised) | 23.33 |
| Soya Bean Oil | 31.10 |
| Soya Lecithin | 1 |
| Fats and Waxes | 4.66 |

The soya lecithin is thoroughly mixed with the soya bean oil, the mixture warmed to 40° C. and the fats and waxes added. The mixture is stirred until the waxes melt and the mix becomes homogeneous. The 2-(carbamoyl)-phenyl-2-acetoxybenzoate is then added slowly with stirring until a uniform slurry is obtained. The mix is then filled into soft gelatin capsules in amounts to provide 350 mg 2-(carbamoyl)phenyl-2-acetoxybenzoate per capsule.

EXAMPLE 5

| Aqueous Suspensions | Gm |
| --- | --- |
| 2-(carbamoyl) phenyl-2-acetoxybenzoate) | 10.0 |

| Aqueous Suspensions | | Gm |
|---|---|---|
| Hydroxyethylcellulose | | 1.0 |
| Sorbitol solution | | 70.0 |
| Citric acid | | 0.1 |
| Sodium lauryl sulphate | | 0.5 |
| Water | to | 100 ml. |

The citric acid, sodium lauryl sulphate and hydroxyethyl cellulose are ground together to give a smooth gel and the 2-(carbamoyl)phenyl-2-acetoxybenzoate is slowly ground in to give a smooth suspension. The volume is made up to 100 ml with water.

| | | Gm |
|---|---|---|
| 2-(Carbamoyl)phenyl-2-acetoxybenzoate | (micronised) | 20 |
| Tragacanth compound | | 2 |
| Water | to | 100 ml. |

The tragacanth is ground up into the water to make a smooth gel. The 2-(carbomoyl)phenyl-2-acetoxybenzoate is then added in small portions and ground in.

The following experiments illustrate (A) the reduced gastric toxicity of 2-(carbamoyl)phenyl-2-acetoxybenzoate relative to a physical mixture of aspirin and salicylamide and (B) the in vivo hydrolysis of 2-(carbamoyl)phenyl-2-acetoxybenzoate to give plasma concentrations of salicylic acid and salicylamide.

(A) Gastric Effects of 2-(carbamoyl)phenyl-2-acetoxybenzoate compared with a physical mixture of aspirin and salicylamide.

Starved rats have been shown to be sensitive to the gastric irritant effects of anti-inflammatory drugs and this model has been used to predict the liability of compounds to exhibit gastric toxicity.

Method

Female Olac Wistar rats, weight range 130–160 g., were fasted for 18 hours prior to dosing with test substances suspended in 0.7% methyl cellulose solution. One hour later the animals were killed, their stomachs excised, inflated with 0.9% saline and allowed to stretch. The stomachs were cut along the greater curvature, pinned out and examined for the presence of erosions of the gastric mucosa.

Doses of compounds were arranged on a milligram molar per kilogram basis, thus 1 mg mole/kg of 2-(carbamoyl)phenyl-2-acetoxybenzoate=299 mg/kg and 1 mg mole/kg of the mixture of aspirin+salicylamide=317.3 mg/kg (180.2+137.1). A range of at least 3 doses per sample were used with a minimum of 8 rats per group.

Results

The proportions of rats showing gastric erosions are given in Table 1. It can be seen that whilst the physical mixture of aspirin with salicylamide produced a marked, dose related incidence of gastric erosions, 2-(carbamoyl)phenyl-2-acetoxybenzoate was free from significant gastric toxicity, as assessed by this model, at all but the highest dose of 2 mg.moles/kg.

Table I

| Test Substance | No. of rats in group | Dose | No. of rats with erosion | % incidence of erosions |
|---|---|---|---|---|
| Physical mixture | 8 | 0.5 | 3 | 37.5% |
| of aspirin and salicylamide | 16 | 1.0 | 6 | 37.5% |
| | 8 | 2.0 | 5 | 62.5% |
| | 8 | 0.5 | 0 | 0% |
| 2-(carbamoyl)phenyl-2-acetoxybenzoate | 8 | 1.0 | 0 | 0% |
| | 8 | 1.5 | 0 | 0% |
| | 8 | 2.0 | 1 | 12.5% |

(B) Salicylic acid and salicylamide plasma levels in dogs

Sixteen dogs (8 male/8 female) were randomly allocated to four groups of four dogs (2 male/2 female per group). Each group was dosed with one of the following test materials at the dose shown:

| | | |
|---|---|---|
| Aspirin | 240 mg/kg | |
| 2-(Carbamoyl)phenyl-2-acetoxybenzoate | 399 mg/kg | All at 1.33 m M/kg |
| Salicylamide | 183 mg/kg | |
| Control | Vehicle only | |

The animals were dosed orally by intubation of 4 ml/kg of a 1% methyl cellulose suspension containing the test materials, one dose per day for 15 days.

On the 15th day of dosing blood samples were taken at t=0, 2, 4, 6 and 24 hours post dosing and assayed by a specific G.L.C. assay for salicylic acid and salicylamide as appropriate.

Table 2 shows the mean (of four dogs) plasma salicylic acid levels obtained by the aspirin and 2-(Carbamoyl)phenyl-2-acetoxybenzoate groups on the 15th day of dosing.

Table 2

| | *0 | 2 | 4 | 6 | 24 |
|---|---|---|---|---|---|
| Aspirin | **86.6 | 261.4 | 246.3 | 202.9 | 41.52 |
| 2-(Carbamoyl)phenyl-2-acetoxybenzoate | 9.6 | 69.7 | 112.5 | 127.9 | 27.9 |

*Hours after dosing
**Micrograms per ml. of salicylic acid in plasma.

Table 3 gives the mean, of four dogs, plasma salicylamide levels obtained by the 2-(carbamoyl)phenyl-2-acetoxybenzoate and salicylamide groups on the 15th day of dosing.

Table 3

| | *0 | 2 | 4 | 6 | 24 |
|---|---|---|---|---|---|
| 2-(Carbamoyl)phenyl-2-acetoxybenzoate | **0.00 | 0.73 | 5.78 | 5.69 | 0.81 |
| Salicylamide | 0.00 | 16.02 | 1.32 | 0.16 | 0.00 |

*Hours after dosing
**Micrograms per ml of salicylamide in plasma

In summary the important points from this study are:

a. free salicylamide has been detected in plasma after administration of 2-(carbamoyl)phenyl-2-acetoxybenzoate. The levels achieved with this dose are similar to levels which have been shown to be pharmacologically active (as a sedative) in man.

b. Free salicylic acid has been detected in plasma after administration of 2-(carbamoyl)phenyl-2-acetoxybenzoate. The levels achieved with this dose are considered greater than those needed to show analgesia and antipyresis in man.

We claim:

1. An orally administrable pharmaceutical composition having analgesic, antipyretic and anti-inflammatory activity upon administration to humans in need thereof in the form of a capsule, pill, tablet, aqueous suspension containing a coloring, flavoring or wetting agent or a powder for addition to and forming such an aqueous suspension, said composition comprising an amount of 2-(carbamoyl)-phenyl-2-acetoxybenzoate effective to produce such activity and one or more pharmaceutically acceptable oral carriers, said (2-carbamoyl-phenyl)2-acetoxybenzoate being stable under the acid pH conditions of the human stomach and being absorbed from the gastro-intestinal tract into the blood where it undergoes hydrolysis to active form and thus avoiding gastric irritation due to aspirin and the inactivation of salicylamide.

2. An orally administrable pharmaceutical composition according to claim 1 wherein the composition is formulated into units for daily dosage.

3. A pharmaceutical composition as claimed in claim 1 in the form of a tablet or powder which effervesces upon addition to water.

4. A method for obtaining analgesic, antipyretic and anti-inflammatory action in human beings in need thereof comprising the oral administration to the humans of an effective amount of 2-(carbamoyl)phenyl-2-acetoxybenzoate.

5. A method as claimed in claim 4 wherein from 4 to 8 gms daily are administered.

6. A method of obtaining the therapeutic effect of administering aspirin orally to human beings without producing gastric irritation due to aspirin and of obtaining the therapeutic effect of administering salicylamide to human beings without causing substantial inactivation of the salicylamide thus administered comprising the oral administration of an analgesic, antipyretic and anti-inflammatory dosage of 2-(carbamoyl)phenyl-2-acetoxybenzoate to human beings in a condition to benefit therefrom.

* * * * *